(12) United States Patent
Hirai et al.

(10) Patent No.: US 6,951,644 B2
(45) Date of Patent: Oct. 4, 2005

(54) ADSORBENT FOR PEPTIDOGLYCAN AND METHOD AND APPARATUS FOR ADSORPTIVELY REMOVING PEPTIDOGLYCAN

(75) Inventors: Fumiyasu Hirai, Ibaraki (JP); Shigeo Furuyoshi, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 10/130,282

(22) PCT Filed: Nov. 30, 2000

(86) PCT No.: PCT/JP00/08487

§ 371 (c)(1),
(2), (4) Date: May 29, 2002

(87) PCT Pub. No.: WO01/39879

PCT Pub. Date: Jun. 7, 2001

(65) Prior Publication Data

US 2003/0003438 A1 Jan. 2, 2003

(30) Foreign Application Priority Data

Dec. 2, 1999 (JP) .......................................... 11/343164
Nov. 7, 2000 (JP) ....................................... 2000/338945

(51) Int. Cl.⁷ ..................... A61K 39/00; A61K 39/395; C07K 1/00
(52) U.S. Cl. .................................... 424/140.1; 530/364
(58) Field of Search ...................... 424/140.1; 530/350, 530/412, 300, 364, 380, 417, 830; 514/2

(56) References Cited

U.S. PATENT DOCUMENTS

| | | | |
|---|---|---|---|
| 4,147,764 A | 4/1979 | Levy et al. ..................... 434/1 |
| 4,576,928 A | 3/1986 | Tani et al. | |
| 4,673,734 A | * 6/1987 | Tayot et al. ................. 530/364 |
| 5,004,711 A | 4/1991 | Grodek ........................ 501/103 |
| 5,122,112 A | 6/1992 | Jones | |
| 5,234,904 A | 8/1993 | Sawada et al. ................. 514/8 |
| 5,407,581 A | * 4/1995 | Onodera et al. ............ 210/654 |
| 5,618,438 A | 4/1997 | Fritz et al. ................... 210/679 |
| 6,322,989 B1 | * 11/2001 | Cohen ........................ 435/7.1 |
| 6,413,729 B1 | 7/2002 | Ashida et al. ............. 435/7.32 |

FOREIGN PATENT DOCUMENTS

| | | |
|---|---|---|
| EP | 993834 | 4/2000 |
| JP | 1-49725 | 10/1989 |
| JP | 2-36211 | 2/1990 |
| JP | 3-8442 | 1/1991 |
| JP | 5-285469 | 11/1993 |
| JP | 10-328565 | 12/1998 |
| WO | WO 98/475484758 | * 10/1998 |

OTHER PUBLICATIONS

Hideo Igarashi et al., "Purification and Characterization of *Staphylococcus aureus* FRI 1169 and 587 Toxic Shock Syndrome Exotoxins", Infection and Immunity, Apr. 1984, p. 175–181.

Zenker et al. "Characterization of Peptiodoglycan Trimers after Gel Chromatography and Reversed–phase HPLC by Positive–ion Desorption Mass Spectrometry" Rapid Communications in Mass Spectrometry, vol. 10, 1956–1960 (1996).

Nishin et al. "Komugi Tailing karano Peptidoglycan no Chuushitsu, Seisei" Nippon Shokuhin Kogyo Gakkaishi, vol. 29, No. 11, 635–641 (1982) with partial translation.

European Search Report dated Mar. 2, 2005.

* cited by examiner

*Primary Examiner*—Jon Weber
*Assistant Examiner*—Sheridan Snedden
(74) *Attorney, Agent, or Firm*—Armstrong, Kratz, Quintos, Hanson & Brooks, LLP

(57) ABSTRACT

An adsorbent for peptidoglycan which comprises an water-insoluble porous material having an amino group and having a molecular weight of exclusion limit of at least 50,000, and a method for removing peptidoglycan by adsorption, which comprises a step of contacting the adsorbent to a liquid containing peptidoglycan.

1 Claim, 2 Drawing Sheets

ADSORBENT FOR PEPTIDOGLYCAN AND METHOD AND APPARATUS FOR ADSORPTIVELY REMOVING PEPTIDOGLYCAN

TECHNICAL FIELD

The present invention relates to an adsorbent, a method for removing by adsorption and an adsorber in order to remove peptidoglycan from a solution containing it. For more detail the present invention relates to an adsorbent, a method for removing by adsorption and an adsorber in order to regulate an excessive immune (inflammatory) reaction by removing peptidoglycan from body fluids.

BACKGROUND ART

Peptidoglycan is a component of the cell wall of bacteria, occupies 40 to 95% of the cell wall in case of Gram-positive bacteria and occupies 10 to 20% of the cell wall in case of Gram-negative bacteria. Peptidoglycan has a various biological activity by itself and causes, for example, shock disease or arthritis. It is also reported that a minimum biological activity unit of peptidoglycan is N-acetylmuramyl-L-alanyl-D-isoglutamine (muramyldipeptide, MDP) and by itself has a biological activity such as increasing a production of cytokines. Therefore, when the peptidoglycane invades into the blood by an infection of bacteria, whereby a severe condition of shock disease or arthritis as mentioned above may be caused. Furthermore, it is suggested that when peptidoglycan coexists with endotoxin, it may causes more severe condition due to a synergistic effect between the two.

In the field of an artificial dialysis of the blood, it is suggested that when peptidoglycan gets mixed in a dialysis solution, it invades into the blood of a patient during the dialysis, and then the same problem may be caused. Although a filter membrane is often used for removing peptidoglycan from the dialysis solution, small peptidoglycan having low morecular weight among all peptidoglycans can filter out though the filter membrane and can not be removed. Because the filter membrane screens based on a molecular weight. Additionally, when the peptidoglycan exists into the body fluid, the filter membrane can not be used substantially, because it removes other components such as protein. Against this background, it is desirable to develop dsorbents capable of efficiently removing peptidoglycan having low molecular weight and furthermore, capable of removing peptidoglycan present in body fluids.

The present invention is made in view of the above-mentioned background, and provides adsorbents capable of efficiently removing peptidoglycan present in a liquid, and a method for removing peptidoglycan present in the liquid and an adsorber for peptidoglycan using thereof.

DISCLOSURE OF INVENTION

The present invention relates to an adsorbent for peptidoglycan being a water-insoluble porous material having an amino group, in which the water-insoluble porous material has a molecular weight of exclusion limit of at least 50,000.

The present invention also relates to a method for removing peptidoglycan, which comprises bringing a liquid containing peptidoglycan into contact with the above-mentioned adsorbent for peptidoglycan.

Further, the present invention relates to an adsorber for removing peptidoglycan comprising a container having an inlet and an outlet for a liquid, and the above-mentioned adsorbent for peptidoglycan packed in the container.

BEST MODE FOR CARRYING OUT THE INVENTION

Figure 1:
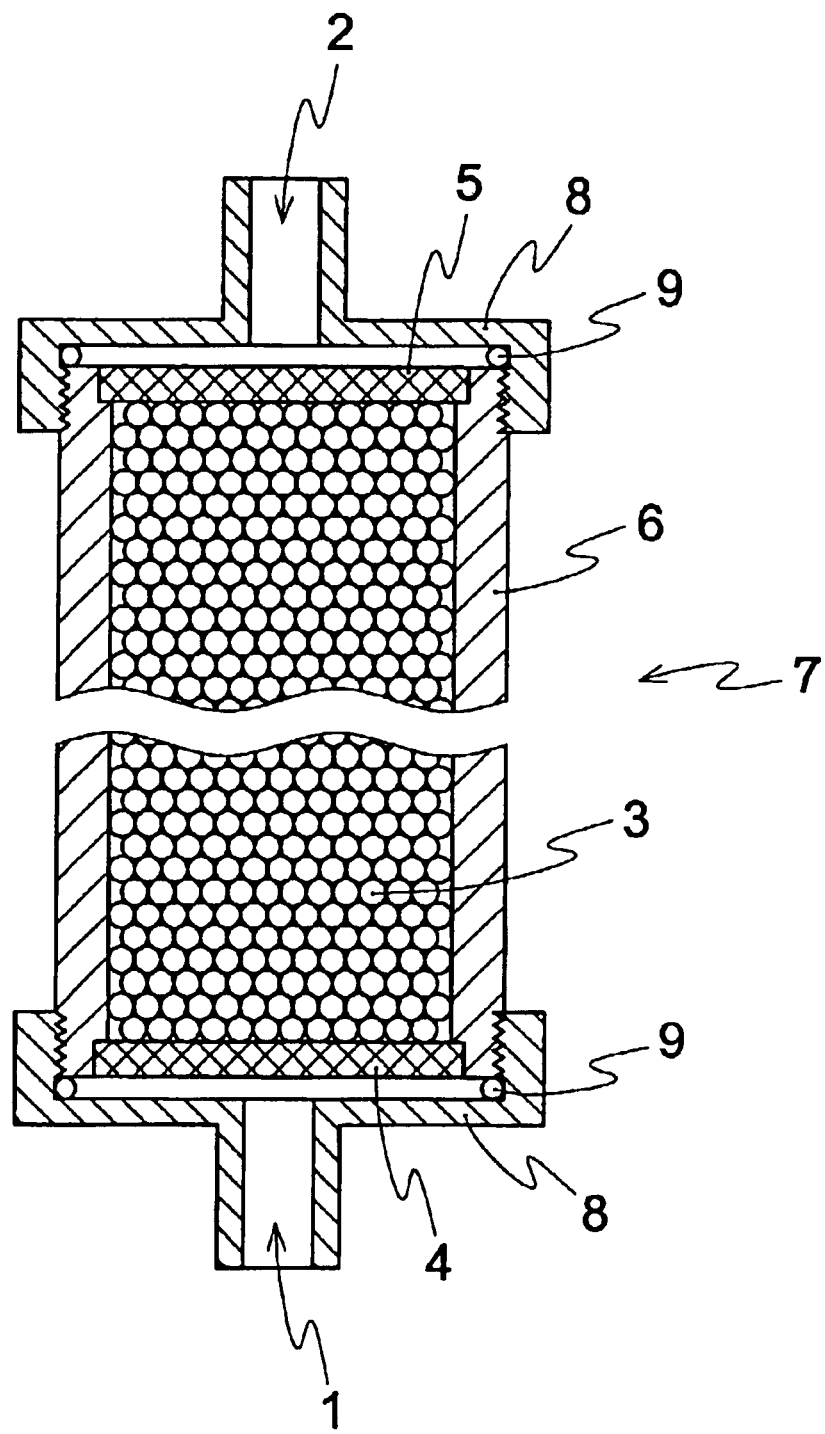
FIG. 1 is a schematic cross section view showing an embodiment of an adsorber for removing peptideglycan according to the present invention using an absorbent for peptideglycan.

Herein, "peptidoglycan" means a polymer, origopeptide which is a component of a cell wall of almost of prokryote such as bacteria. Peptideglycan is characterized by having N-acetylmuramic acid or N-plycosylmuramic acid, and D-amino acid.

The term "liquid" in the present invention includes, for example, water, buffer and the body fluid, the body fluid is preferable. Also, the term "body fluid" means blood, plasma, serum, ascites, lymph, synovia and fractions obtained from them, and liquid components derived from other living body.

In accordance with the present invention, an amino group includes a secondary amino group represented by —$NHR^1$; a tertiary amino group represented by —$NR^1R^2$; a quaternary ammonium base represented by —$N^+R^1R^2R^3.X^-$; as well as a primary amino group represented by —$NH_2$; wherein $R^1$, $R^2$ and $R^3$ are an atomic group exclusive of hydrogen atom, for example, an alkyl group having 1 to 10 carbon atoms such as methyl group or ethyl group, an aryl group such as phenyl group, or the like; $X^{31}$ is an anion. $R^1$, $R^2$ and $R^3$ may be the same group or different group.

The "water-insoluble" in the present invention means a material which is solid at ordinary temperature under ordinary pressure, and water-solubility of which is extremely low.

A water-insoluble porous material having an amino group in the present invention includes (1) a water-insoluble porous material having an amino group intrinsically, (2) a water-insoluble porous material obtained by polymerizing a monomer having an amino group, (3) a material obtained by immobilizing a compound having an amino group to a water-insoluble porous material, but is not limited thereto.

The above water-insoluble porous material having an amino group intrinsically (1) includes, for example, chitosan, a derivative thereof and the like. In accordance with the present invention, the water-insoluble porous material having an amino group intrinsically also includes a material obtained by treating such as cross-linking a water-soluble compound among a polymer material having an amino group intrinsically in order to be water-insoluble. Examples of such compound are polyamine such as cardohexamine, N-desulfate heparitin sulfate, N-desulfate heparin and the like.

In the above water-insoluble porous material obtained by polymerizing a monomer having an amino group (2), examples of the monomer include ethyleneimine, allylamine, vinylamine, propyleneamine, aminomethyl methacrylic ester, lysine and the like. Such monomers can be used by polymerizing alone, or by copolymerizing in an optional combination of two or more thereof, in an optional combination with a monomer not having an amino group or with a cross-linker. As the monomer, any material can be used without particular limitation as long as it becomes water-insoluble by polymerization or copolymerization.

In the above material obtained by immobilizing a compound having an amino group to a water-insoluble porous material (3), examples of the compound having an amino group are an alkylamine such as ammonia, methylamine, ethylamine, propylamine, butylamine, t-butylamine, hexylamine, octylamine, decylamine, dodecylamine or hexadecylamine; an amino acid such as histidine or lysine; a diamine such as ethylenediamine or hxamethylenediamine; a primary amine such as monoethanolamine; a secondary amine such as dimethylamine, diethylamine or methylethylamine; and a tertiary amine such as trimethylamine, triethylamine, tributylamine, dimethylpropanolamine, dimethylethanolamine, 1-dimethylamino-2,3-propanol or methyldiethanolamine. But it is not limited to these compounds.

Typical examples of the water-insoluble porous material in the present invention are inorganic material such as glass beads and silica gel; organic material comprising synthetic polymers or polysaccharides; and composite material each comprising a combination of the above-mentioned materials such as organic-organic material and organic-inorganic material.

Any monomer of synthetic polymers can be used without particular limitation as long as it is capable of copolymerizing. Examples of such monomer are styrene, acrylic acid, methacrylic acid, acrylonitrile, acrylic ester, methacrylic ester, vinylpyridine, glycidyl methacrylate, dimethylaminoethyl methacrylate, acrylamide, methacrylamide, vinyl acetate, vinyl alcohol, vinyl chloride and the like, but not limited thereto. Additionally, a bridged compound obtained by copolymerizing each monomer with, for example, divinylbenzen can be also used.

The above-mentioned polysaccharides include crystalline cellulose, cellulose, agarose, dextrin, chitosan and the like, but not limited thereto.

When an adsorbent is used for adsorbing peptidoglycan from the liquid with many contaminant such as the body fluid, hydrophilic porous materials among the water-insoluble porous materials are preferable since non-specific adsorption is comparatively a little and the adsorption selectivity for peptidoglycane is good.

The term "hydrophilic porous material" as used herein refers to a material composed of a compound which has a contact angle with water of 60 degrees or less when the compound is shaped into a flat plate. Various methods for measuring the contact angle with water are known, but the most general is a method wherein a water droplet is placed on a plate made of a compound to be measured and the contact angle is measured, as shown in Ikeda, Jikken Kagaku Sensho, Colloid Chemistry, Chapter 4, Thermodynamics of Interface, pages 75–104 (1986) published by Shokabo, Japan. Typical examples of such hydrophilic material which are made of a compound having a contact angle with water of at most 60 degrees as measured by this method are, for instance, those comprising cellulose, polyvinyl alcohol, hydrolyzed ethylene-vinyl acetate copolymer, polyacrylamide, polyacrylic acid, polymethacrylic acid, polymethylmethacrylate, polyacrylic acid-grafting polyethylene, polyacrylamide-grafting polyethylene, glass and the like.

However, when peptidoglycan is adsorbed from the liquid with small cintaminant such as water or buffer, hydrophobic water-insoluble porous materials can be practically used as well as hydrophilic water-insoluble porous materials.

Peptidoglycan has a molecular weight of approximately 500 in MDP that is a minimum biological activity unit. However, it is reported that peptidoglycan exists in form of an enormous network molecule in general. The adsorbents for peptidoglycan in the present invention have a large number of pores having an adequate size, namely a porous structure. The term "material having a porous structure" comprehends, to say nothing of a material each particle of which comprises fine primary particles of a macromolecular material agglomerated to form a globular particle and has spaces (macropores) between the agglomerated primary particles, a material each particle of which is an agglomerate of porous primary particles of a macromolecular material having fine pores (micropores), and a material each particle of which is made of a copolymer having a three-dimensional network structure (polymer network) and contains fine pores (micropores) formed when swollen with an organic solvent having an affinity with the copolymer. Further, from the viewpoint of the adsorption capacity per unit volume of an adsorbent, the water-insoluble porous material having a porous structure is preferred to be porous throughout the entire body rather than only in the surface region. It is also desirable that the pore volume and specific surface area of the material are as large as possible so long as the adsorption ability is not impaired.

An evaluation of a pore size of a water-insoluble porous material can be carried out by measuring a molecular weight of exclusion limit thereof. The term "molecular weight of exclusion limit" means the molecular weight of the smallest molecule of molecules which cannot enter fine pores (namely which are excluded) in a gel permeation chromatography, as described in books (see, for example, Hiroyuki Hatano and Toshihiko Hanai, "Experimental High Performance Liquid Chromatography", Kagaku Dojin). In general, the molecular weight of exclusion limit has been well examined with use of globular protein, dextran, polyethlene glycol or the like. In the case of the water-insoluble porous material used in the present invention, the molecular weight of exclusion limit is preferably at least 60,000, more preferably at least 70,000, for the reason that the molecular weight of exclusion limit for globular protein is at least 50,000 and further that higher molecular weight fraction of peptidoglycan can be adsorbed.

Meanwhile, when a hydrophobic water-insoluble porous material such as styrene divinylbenzen copolymer is employed as the water-insoluble porous material, an accurate molecular weight of exclusion limit can not be determined because of non-specific adsorption of the substance used for measuring the molecular weight of exclusion limit. In such case, the mode of pore size can be measured using mercury porosimetry method or nitrogen adsorption method in dry state. When the volume of the adsorbent is decreased due to contraction occurred from the dryness, it is necessary to correct corresponding to the contraction. For instance, when the volume of adsorbent becomes one-Ath, it is necessary to correct the measured value multiplied by third root of A. The relation between the mode of the pore size and the molecular weight of exclusion limit for the globular protein is not defined. However, the diameter of globular protein used for measuring the molecular weight of exclusion limit has been determined, for example, that of chymotrypsinogen A having a molecular weight of 25,000 is about 42 Å, that of ovalbumin having a molecular weight of 43,000 is about 61 Å, that of albumin having a molecular weight of 67,000 is about 71 Å. Therefore, for globular protein, the molecular weight of exclusion limit of at least 50,000 in the present invention corresponds to about at least 65 Å of the diameter.

Furthermore, in the above materials obtained by immobilizing a compound having an amino group to a water-insoluble porous material (3), it is preferable that the water-insoluble porous material has a functional group which can be used in a immobilization reaction of the compound having an amino group. Typical examples of the functional group are, for instance, hydroxyl group, amino group, aldehyde group, carboxyl group, thiol group, silanol group, amide group, epoxy group, halogen, succinimide group, acid anhydride group, phenyl group and the like. The functional groups are not limited to the exemplified groups.

Any of a hard material and a soft material can be used as the material in the present invention. In the case of use as an adsorbent for an extracorporeal circulation, it is important that the adsorbent does not clog up when it is charged in a column and a fluid is passed through the column. For this purpose, a sufficient mechanical strength is required for the adsorbent. Accordingly it is more preferable that the material used in the present invention is a hard material.

The term "hard material" as used herein refers to, for example, in the case of a granular material, a material which has such a property that a linear relation between pressure drop $\Delta P$ and flow rate is held up to a pressure drop of 0.3 $kg/cm^2$ when the material is uniformly charged in a cylindrical column and an aqueous fluid is passed through it, as shown in Reference Example described after.

A typical example of the material which satisfies these desirable requirements is a porous cellulose material. The porous cellulose material has the superior properties that (a) the material is hard to be destroyed or to become fine powder by an operation such as agitation because it has a comparatively high mechanical strength and toughness, so when the material is packed in a column, compaction and choking of the column do not occur even if a body fluid is flowed at a high flow rate, thus enabling to flow a body fluid at a high rate, and further the porous structure is hard to change by a high pressure steam sterilization or the like, (b) since the material is made of a cellulose, it is hydrophilic, and many hydroxyl groups which can be utilized for bonding a ligand are present, and non-specific adsorption hardly occurs, (c) the adsorption capacity which is comparable to a soft material can be obtained because the strength is comparatively high even if the pore volume is made large, and (d) the safety is higher than synthetic polymer materials and the like.

Accordingly, a porous cellulose material is one of the most suitable materials, but is not limited thereto. The above-mentioned materials may be used alone or in optional combination of at least 2 kinds thereof.

The water-insoluble porous material in the present invention may be in the form of, for example, particle, board, fiber, hollow fiber, and the like, but the form thereof is not limited thereto. The size of the material is not also particularly limited.

There are various methods for adsorbing and removing peptidoglycan from a liquid by using the adsorbent of the present invention. The most simple method is a method wherein a liquid is taken out and placed in a bag or the like and the adsorbent is mixed therewith to allow to adsorb peptidoglycan and then the adsorbent is filtered off to obtain the liquid from which peptidoglycan has been removed. Another method is a method wherein the adsorbent is packed in a container which has an inlet and an outlet for a liquid and which is equipped at the outlet with a filter which can pass a liquid but cannot pass the adsorbent, and the liquid is passed through the container. Both methods can be used, but the latter method is adequate for the adsorbent of the present invention, since the operation is simple and peptidoglycan can be removed efficiently in on-line system from a body fluid, especially blood, of a patient by incorporating the method into an extracorporeal circulation circuit.

In the extracorporeal circulation circuit as herein referred to, the adsorbent of the present invention can be used not only singly but also in combination with other extracorporeal circulation therapy systems. An example of the combination use includes an artificial dialysis circuit or the like, and the adsorbent can be used in a combination with dialysis therapy.

An adsorber for peptidoglycan of the present invention using the peptidoglycan adsorbent mentioned above will be explained below with reference to FIG. 1 which is a schematic section view showing an embodiment of the adsorber. In FIG. 1, 1 denotes an inlet for a liquid, 2 denotes an outlet for the liquid, 3 denotes the peptidoglycan adsorbent of the present invention, 4 and 5 denote a filter which can pass a liquid and components included therein but cannot pass the adsorbent, 6 denotes a column, 7 denotes an adsorber for peptidoglycan, 8 denotes a holding device, and 9 denotes a packing. The peptidoglycan adsorber of the present invention is not limited to such an exemplified adsorber, and any devices can be used so long as the devices have a structure that the adsorbent mentioned before is packed in a container having an inlet and an outlet for a liquid, and it is more preferable that the adsorber is equipped with a means for preventing the adsorbent from flowing out of the container.

Examples of the means for preventing the adsorbent from flowing out are, for instance, filters such as mesh, nonwoven fabric and cotton stopper. There is no particular limitation in the shape, material and size of the container, but regarding the shape of the container, a cylindrical container is preferred. Preferable materials of the container are those having a sterilization-resistance. Typical examples of such materials are, for instance, glass coated with a silicone, polypropylene, polyvinyl chloride, polycarbonate, polysulfone, polymethylpentene and the like. It is also preferable that the container has a capacity of 50 to 1,500 ml and a diameter of 2 to 20 cm, especially a capacity of 100 to 800 ml and a diameter of 3 to 15 cm, more especially a capacity of 150 to 400 ml and a diameter of 4 to 10 cm.

The present invention is more specifically described and explained by means of the following Examples, but it is to be understood that the invention is not limited to only these Examples.

REFERENCE EXAMPLE

Cylindrical glass columns (inner diameter 9 mm, length 150 mm) equipped with filters having a pore size of 15 $\mu$m at both ends, were charged uniformly with each of an agarose material (BioGel A-5m made by Bio-Rad Laboratories, U.S.A., particle size 50 to 100 meshes), a vinyl polymer material (TOYOPEARL HW-65 made by TOSOH Corporation, Japan, particle size 50 to 100 $\mu$m) and a cellulose material (CELLULOFINE GC-700 m made by Chisso Corporation, Japan, particle size 45 to 105 $\mu$m). The relationship between flow rate and pressure drop $\Delta P$ was determined by passing water through the column with a peristatic pump. The results are shown in FIG. 2.

Figure 2:
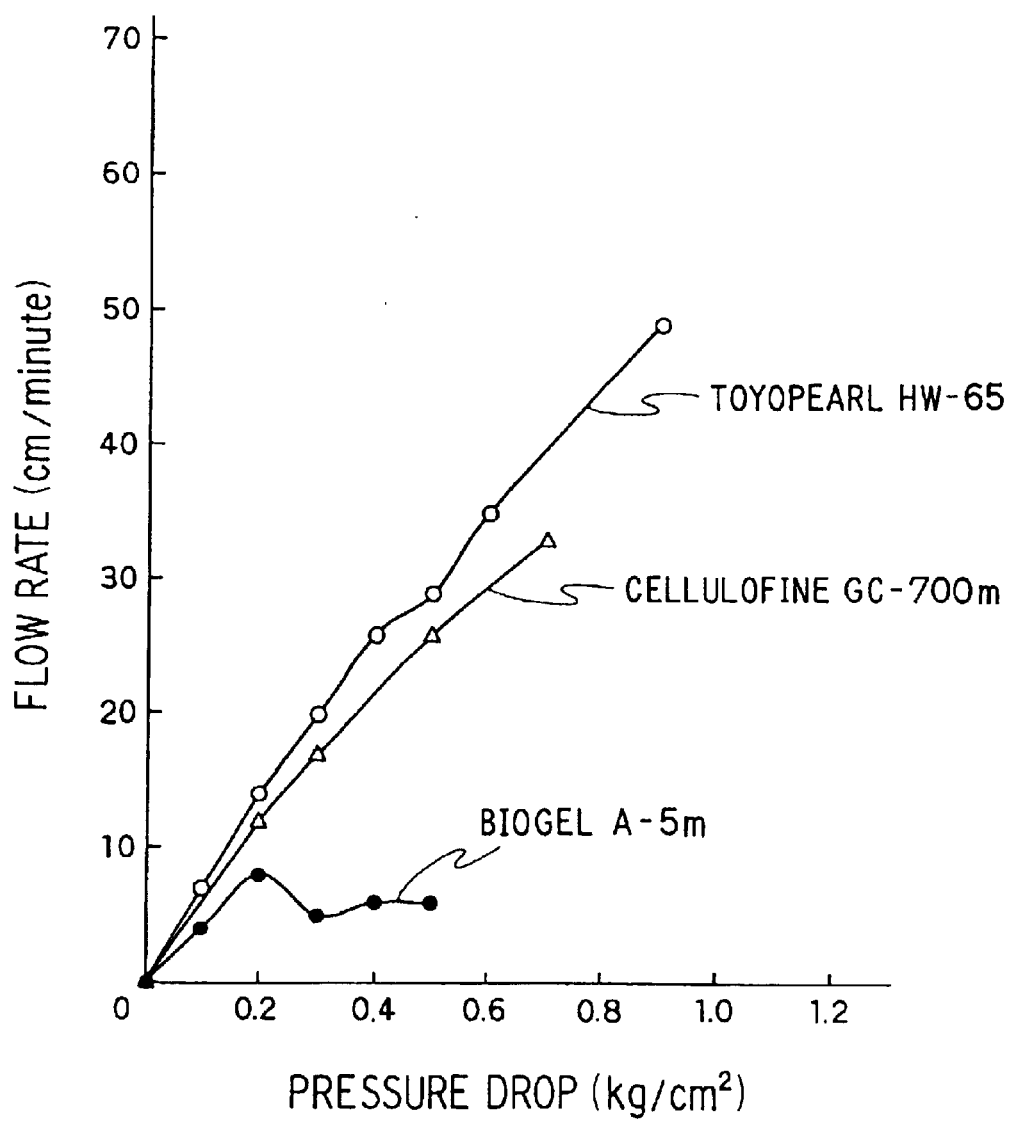
FIG. 2 is a graph showing results of examining a relationship between the flow rate and the pressure drop by using three kinds of gels.

In FIG. 2, it is found that TOYOPEARL HW-65 and CELLULOFINE GC-700 m show that the flow rate increases almost in proportion to an increase in pressure, whereas BioGel A-5m causes a compaction and the flow rate does not increase even if the pressure is increased. In the present invention, a material showing that the relationship between the pressure drop ΔP and the flow rate is linear up to a pressure drop of 0.3 kg/cm$^2$, like the former, is referred to as a hard material.

EXAMPLE 1

To a test tube was added 0.2 ml of a porous material comprising styrene-divinylbenzene copolymer having a quaternary ammonium base: IRA938 (anion-exchange resin made by ORGANO CORPORATION: the mode of pore size: at least 25,000 Å, and molecular weight of exclusion limit for globular protein: at least 50,000), and was replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing IRA938. The content of this test tube was mixed and shaken at 37° C. for 2 hours. After the shaking, a concentration of peptidoglycan in a supernatant was determined using the SLP (available from Wako Pure chemical Industries, Ltd.) method.

COMPARATIVE EXAMPLE 1

To a test tube was added 0.2 ml of a porous material comprising styrene-divinylbenzene copolymer having a sulfonic acid group: RCP160 (cation-exchange resin made by MITUBISHI CHEMICAL CORPORATION: the mode of pore size: 200 Å, and molecular weight of exclusion limit for globular protein: at least 50,000), and was replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing RCP160. The content of this test tube was mixed and shaken at 37° C. for 2 hours. After the shaking, a concentration of peptidoglycan in a supernatant was determined using the SLP (available from Wako Pure chemical Industries, Ltd.) method.

COMPARATIVE EXAMPLE 2

To a test tube was added 0.2 ml of a porous material comprising styrene-divinylbenzene copolymer: HP20 (cation-exchange resin made by MITUBISHI CHEMICAL CORPORATION: the mode of pore size: 200 Å, and molecular weight of exclusion limit for globular protein: at least 50,000), and was replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing HP20. The content of this test tube was mixed and shaken at 37° C. for 2 hours. After the shaking, a concentration of peptidoglycan in a supernatant was determined using the SLP (available from Wako Pure chemical Industries, Ltd.) method.

The results of Example 1, and Comparative Example 1 and 2 are shown in Table 1.

TABLE 1

|  | Concentration of Peptidoglycan in the supernatant |
| --- | --- |
| Example 1 | 0.09 ng/ml |
| Comparative Example 1 | 8.75 ng/ml |
| Comparative Example 2 | 9.98 ng/ml |

In table 1, it is found that in Example 1 the concentration of Peptidoglycan in the supernatant is decreased widely compared with that of Comparative Example 1 and 2.

EXAMPLE 2

Water was added to 170 ml of a porous cellulose material: CK (made by Chisso Corporation, Japan, molecular weight of exclusion limit for a globular protein: at least 50,000,000) up to the total amount of 340 ml. Thereto was added 90 ml of 2M aqueous solution of sodium hydroxide, and the mixture was kept at 40° C. To the mixture was then added 31 ml of epichlorohydrin, and the reaction was carried out with stirring at 40° C. for 2 hours. After the completion of the reaction, the material was thoroughly washed with water to give an epoxidized CK.

To 10 ml of the epoxidized CK was added 200 mg of n-butylamine, and ethanol was added thereto up to the total amount of 20 ml. The mixture was allowed to stand for reaction in ethanol at 45° C. for 6 days to immobilize. After the completion of the reaction, the material was thoroughly washed with ethanol and water in that order to give n-butylamine-immobilized CK.

To a test tube was added 0.2 ml of the obtained n-butylamine-immobilized CK, and replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing n-butylamine-immobilized CK. The content of this test tube was mixed and shaken at 37° C. for 2 hours. After the shaking, a concentration of peptidoglycan in a supernatant was determined using the SLP (available from Wako Pure chemical Industries, Ltd.) method.

EXAMPLE 3

Except for using n-hexdecylamine as a substitute for n-butylamine, an n-hexadecylamine-immobilized CK was prepared in the same manner as in Example 2.

To a test tube was added 0.2 ml of the obtained n-hexadecylamine-immobilized CK, and replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing n-hexadecylamine-immobilized CK. The content of this test tube was mixed and shaken at 37° C. for 2 hours. After the shaking, a concentration of peptidoglycan in the supernatant was determined using the SLP (available from Wako Pure chemical Industries, Ltd.) method.

COMPARATIVE EXAMPLE 3

To a test tube was added 0.2 ml of the CK, and replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing the CK. The content of this test tube was mixed and shaken at 37° C. for 2 hours. After the shaking, a concentration of peptidoglycan in the supernatant was determined using the SLP (available from Wako Pure chemical Industries, Ltd.) method.

The results of Example 2 and 3, and Comparative Example 3 are shown in Table 2.

TABLE 2

|  | Concentration of Peptidoglycan in the supernatant |
|---|---|
| Example 2 | 0.05 ng/ml |
| Example 3 | 0.02 ng/ml |
| Comparative Example 3 | 9.34 ng/ml |

In table 2, it is found that in Example 2 and 3 the concentration of Peptidoglycan in the supernatant is decreased widely compared with that of Comparative Example 3.

EXAMPLE 4

Except for using a porous cellulose material: GC100 m (made by Chisso Corporation, Japan, molecular weight of exclusion limit for a globular protein: at least 60,000) as substitute for CK, n-hexadecylamine-immobilized GC100m was prepared in the same manner as in Example 3.

To a test tube was added 0.2 ml of the obtained n-hexadecylamine-immobilized GC100 m, and replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing the n-hexadecylamine-immobilized GC100m. The content of this test tube was mixed and shaken at 37° C. for 2 hours. After the shaking, a concentration of peptidoglycan in the supernatant was determined using the SLP (available from Wako Pure chemical Industries, Ltd.) method.

COMPARATIVE EXAMPLE 4

To a test tube was added 0.2 ml of the GC100 m, and replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing the GC100m. The content of this test tube was mixed and shaken at 37° C. for 2 hours. After the shaking, a concentration of peptidoglycan in the supernatant was determined using the SLP (available from Wako Pure chemical Industries, Ltd.) method.

COMPARATIVE EXAMPLE 5

The marketed cellulose acetate is dissolved in a mixed solvent of dimethyl sulfoxide and propylene glycol. A drop consisting of the mixture solution is formed and coagulated to obtain a spherical porous material comprising cellulose acetate using the method described in JP 63-117039 (vibration method). This material is mixed with aqueous solution of sodium hydroxide, the dehydration reaction is carried out to obtain a cellulose porous material (average particle size: 460 $\mu$m, molecular weight of exclusion limit for globular protein: 20,000). Except for using the obtained porous cellulose material herein as substitute for CK, n-hexadecylamine-immobilized material was prepared in the same manner as in Example 3.

To a test tube was added 0.2 ml of the obtained n-hexadecylamine-immobilized material, and replaced and washed with distilled water sufficiently. Thereafter the excess supernatant was removed. Peptidoglycan (from *Micrococcus luteus*, available from Wako Pure chemical Industries, Ltd.) was dissolved in distilled water to obtain peptidoglycan solution in concentration of about 9 ng/ml. The peptidoglycan solution in amount of 1.2 ml was added to the test tube containing the n-hexadecylamine-immobilized material. The content of this test tube was mixed and shaken at 37° C. for 2 hours. After the shaking, a concentration of peptidoglycan in the supernatant was determined using the SLP (available from Wako Pure chemical Industries, Ltd.) method.

The results of Example 4, and Comparative Example 4 and 5 are shown in Table 3.

TABLE 3

|  | Concentration of Peptidoglycan in the supernatant |
|---|---|
| Example 4 | 0.01 ng/ml |
| Comparative Example 4 | 8.75 ng/ml |
| Comparative Example 5 | 5.24 ng/ml |

In table 3, it is found that in Example 4 the concentration of Peptidoglycan in the supernatant is decreased widely compared with that of Comparative Example 4 and 5.

INDUSTRIAL APPLICABILITY

Peptidoglycan can be efficiently adsorbed and removed from the body fluid by the adsorbent for peptidoglycan of the present invention characterized in that it comprises a water-insoluble porous material having an amino group and that the water-insoluble porous material has a molecular weight of exclusion limit of at least 50,000.

What is claimed is:

1. A method for removing peptidoglycan, which comprises bringing blood containing peptidoglycan into contact with an adsorbent for peptidoglycan comprising a water-insoluble porous material consisting essentially of an organic material selected from the group consisting of a synthetic polymer and a polysaccharide, wherein an amino group is attached to said water-insoluble porous material with covalent bond, and having a molecular weight of exclusion limit of at least 50,000 and thereby removing peptidoglycan from said blood, wherein after peptidoglycan is removed from the blood, the treated blood, containing a reduced amount of peptidoglycan, is returned to the body in an extracorporeal circulation system.

* * * * *